United States Patent [19]

Siewert et al.

[11] 4,375,514
[45] Mar. 1, 1983

[54] PREPARATION AND USE OF RECOMBINANT PLASMIDS CONTAINING GENES FOR ALKALINE PHOSPHATASES

[75] Inventors: Gerhard Siewert; Werner Boidol; Joachim Daum, all of Berlin, Fed. Rep. of Germany

[73] Assignee: Schering, Aktiengesellschaft, Berlin and Bergkamen, Fed. Rep. of Germany

[21] Appl. No.: 174,316

[22] Filed: Aug. 1, 1980

[30] Foreign Application Priority Data

Aug. 3, 1979 [DE] Fed. Rep. of Germany ....... 2931999

[51] Int. Cl.³ .................... C12N 15/00; C12N 1/20; C12N 1/00; C12N 9/16
[52] U.S. Cl. .................... 435/172; 435/91; 435/196; 435/253; 435/317; 435/820; 435/849; 435/881
[58] Field of Search .................... 435/68, 70, 71, 91, 435/196, 172, 253, 317, 820, 849, 881

[56] References Cited

U.S. PATENT DOCUMENTS 4,190,495 2/1980 Curtiss ............................ 435/849 X
4,237,224 12/1980 Cohen et al. ................... 435/820 X

OTHER PUBLICATIONS

Bhatti, "Distinctive Characteristics of the Alkaline Phosphatase of *Serratia Marcescens*", *Chem. Abstracts*, vol. 83, No. 13 (1975), p. 224, Abs. No. 110308c.
Morriss et al., "Pheotriorn Effects of Mutations Involved in the Regulation of *Escherichia coli* K-12 Alkaline Phosphatase", *J. Bact.*, vol. 119, No. 2, (1974), pp. 583-592.
Bracha, et al., "Location of the Genes Controlling Alkaline Phosphatase on F'13 Episone of Escherichia coli", *J. Bact.*, vol. 120, No. 2 (1974), pp. 970-973.
Goebel et al., "Class of Small Multicopy Plasmids Originating from the Mutant Antibiotic Resistance Factor" R1 drd-19B2, *J. Bact.*, vol. 123, No. 2, (1975), pp. 658-665.
Mercereau-Puijalon et al., "Synthesis of an Ovalbumin-Like Protein by *Escherichia coli* K12 Harbouring a Recombinant Plasmid", *Nature*, vol. 275, (1978), pp. 505-510.
Crosa et al., "Construction and Characterization of New Cloning Vehicles", *Gene*, vol. 2, (1977), pp. 95-113.

*Primary Examiner*—Thomas G. Wiseman
*Attorney, Agent, or Firm*—Millen & White

[57] ABSTRACT

PhoA mutant *E. coli* SB44, prepared by mutation of *E. coli* HB101 with an N-nitroso compound, can be used to identify and isolate recombinant plasmids into which a phoA gene has been incorporated. These plasmids can be used to transform bacteria which can be cloned and incubated to provide alkaline phosphatase in high yield. Moreover, these plasmid vectors can be modified in various ways so that the N-terminal amino acid sequence of phoA is followed in reading phase by the DNA coding for some other protein. In turn, these new plasmids can be used to transform bacteria which can be cloned and incubated to produce fusion proteins comprising the desired other protein in high yield and outside of the cell membrane in the periplasmatic space.

46 Claims, 3 Drawing Figures pSB53
MG 8620 Bp
Phenotype
Ap⁺Tc⁻Pho⁺ pSB86
MG 5770 Bp
Phenotype
Ap⁺Tc⁺Pho⁻ pSB87
MG 5970 Bp
Phenotype
Ap⁻Tc⁺Pho⁻

PREPARATION AND USE OF RECOMBINANT PLASMIDS CONTAINING GENES FOR ALKALINE PHOSPHATASES

BACKGROUND OF THE INVENTION

The present invention relates in one aspect to bacterial strains and their preparations, the strains being capable of forming an alkaline phosphatase of the same species or also of a foreign species in greatly increased yields (as compared to the corresponding wild type). They are thus especially well suited for the fermentative production of these enzymes.

Processes for the isolation of alkaline phosphatases from bacteria are known from the monograph "The Enzymes", Ed. P.D. Boyer, Acad. Press (1971) IV: 373-415.

A plasmid is known having an E. Coli phosphatase gene which has an F' factor involved. It is produced by in vivo recombination of a fertility factor with a section of chromosomal DNA in E. Coli [M. Bracha, E. Yagil, J. Bacteriol. 120: 970-973 (1974)]. The isolation of such a plasmid has been described heretofore merely for the E. Coli phosphatase gene and does not represent a generally applicable method for the cloning of phosphatase genes. In particular, it is impossible in this way to clone genes of a quite different origin, e.g., from lower eucaryotes. The F'13 plasmid is present, as many other fertility factors, only in 1-2 copies per cell, whereby, also, only a minor stimulation of phosphatase formation is effected.

Alkaline phosphatases (EC3.1.3.1) are enzymes produced by a plurality of procaryotic and eucaryotic organisms. They are capable of hydrolyzing a great variety of phosphoric acid monoesters to the inorganic phosphate and the corresponding alcohol [Summary by T. W. Reid and I. B. Wilson in "The Enzymes" Ed. P.D. Boyer, Acad. Press (1971) IV: 373-415]. They are used in biochemical and molecular-biological research as well as in clinical diagnostics as preparative and analytical reagents.

DOS No. 2,617,350, for example, discloses a carrier-fixed alkaline phosphatase used in the production of defined oligonucleotides. A quantitative determination of phosphoric acid monoesters is possible by measuring the inorganic phosphate formed in the hydrolysis with alkaline phosphatase [Acta Chem. Scand. B31: 125-129 (1977)]. Another important application is the use of alkaline phosphatase as a readily detectable labeling enzyme in various enzyme immunoassays wherein it is coupled, depending on the type of analysis, to an antigen as well as to antibodies. Enzyme immunoassays permit a specific and quantitative determination of numerous substances (hormones, viral proteins, various cell wall antigens, antibodies, etc.) in minimal amounts [E. Engvall, A. J. Pesce, ed., "Quantitative Enzyme Immunoassay" Blackwell Scientific Publications, Oxford (1978)].

Alkaline phosphatase from E. coli is preferably utilized for many of these applications, wherein, inter alia, the high temperature stability of this enzyme (20 minutes at 85° C.) as compared with mammalian phosphatases is of advantage (Japanese Patent J5 No. 2099-211).

Some bacteria, especially E. coli, synthesize individual enzymes in greatly increased amounts, if numerous copies of the corresponding gene per cell are present. Normally, the gene occurs only once per cell in wild-type bacteria [I. G. Young et al, "Gene" 4: 25-36 (1978)]. This high gene copy number (about 10-20 copies per cell) is attained by selectively transferring DNA fragments carrying the respective gene to bacteria with the aid of the techniques for in vitro recombination of DNA.

Various methods for the controlled transfer of genes to bacteria, also called DNA cloning, have been described in K. N. Timmis, S. N. Cohen, F. C. Caballo, "Progress in Molecular and Subcellular Biology", F. E. Hahn ed., 6: 1-58, Springer publishers (1978) whose disclosure is incorporated by reference herein. They are all based on the procedure of linking a DNA fragment carrying the respective gene to a vector DNA. It is then introduced in this form into a suitable receptor cell and replicated therein as recombinant DNA. Plasmids or bacteriophages serve as vectors. Plasmids are ring-shaped, double-strand DNA molecules found in some strains of bacteria. They are capable of replication therein independently of the chromosomal DNA (extra-chromosomally). Essential aids in the cloning of DNA are the restriction endonucleases capable of sectioning double-strand DNA molecules into smaller fragments at exactly defined sites.

A frequently utilized process for the cloning of DNA fragments carrying genes for metabolic enzymes comprises, for example, reacting chromosomal DNA of a suitable donor organism and plasmid DNA with a suitable restriction endonuclease. The resultant fragments are then intermixed with DNA ligase, thus forming a plurality of different linear and circular, oligomeric products from the DNA fragments. Inter alia, these include ring molecules containing, per plasmid molecule, one molecule of the DNA fragment with the sought-after gene. The DNA mixture is then transferred in a process called transformation to suitable receptor bacteria. From the entire cell population, there are selected cells which contain the sought-after, recombined plasmid DNA. Variations of this procedure involve, for example, fragmenting of the chromosomal DNA by shear forces (ultrasound, etc.) and/or coupling of the DNA fragment to the plasmid via homopolymeric DNA single-strand termini produced with the enzyme terminal transferase [L. Clarke and J. Carbon, "Proc. Nat. Acad. Sci." (USA) 72: 4361-4365 (1975)]. Phage DNA has also been used successfully for cloning instead of plasmids.

In the technique of recombining DNA, especially when starting with a complex mixture of chromosomal DNA fragments, a large number of various hybrid molecules is usually produced in vitro. Therefore, a method of selecting a particular hybrid is required to enable cloning of defined DNA fragments, making it possible, after transformation and/or transfer, to isolate cell clones with the sought-after recombined DNA. If the fragment to be cloned carries a metabolic gene expressible in the receptor organism, then well-transformable mutants can be used as the recipients. These mutants contain the respective gene in inactivated form. Thus, they will exhibit the corresponding metabolic feature (i.e., will express the gene) only after they have absorbed the gene by transformation with recombined DNA in a replicatable form and thus in a form transmittable hereditarily. Accordingly, only those transformed mutant clones which in fact do express the desired gene under conventional translation conditions will have been transformed with the desired recombinant plasmid. The phosphatase-negative mutants of E. coli described in J. Bacteriol. 119: 583–592 (1974), in contradistinction to these required for the above purposes, involve strains which are poorly transformable due to their maintained capability for in vivo recombination. They are thus unsuitable for the cloning of phosphatase genes.

SUMMARY OF THE INVENTION

Accordingly, it is an object of this invention to provide processes and the requisite biochemical entities by which an alkaline phosphatase gene (phoA) of a donor organism can be recombined into a plasmid and the plasmid can be identified and isolated, as well as by which the plasmid can be used to express alkaline phosphatase or can be modified to express fusion proteins in high yields available in the cytoplasm of host transformed bacteria.

Upon further study of the specification and appended claims, further objects and advantages of this invention will become apparent to those skilled in the art.

These objects have been attained by one aspect of this invention by providing phoA mutant E. coli SB44 and a process for preparing it by mutating E. coli SB44 with an N-nitroso compound.

In another aspect, they have been attained by providing plasmid vectors containing a DNA sequence (phoA) coding for alkaline phosphatase, and plasmid vectors containing a DNA sequence which codes a polypeptide sequence of an alkaline phosphatase, the polypeptide sequence containing the N-terminal amino acid of the alkaline phosphatase. These plasmids are prepared by a method for preparing plasmids containing a phoA gene, comprising reacting an antibiotic-resistant plasmid and chromosomal DNA from a wild-type bacteria with a restriction endonuclease, linking the terminal sites with DNA ligase, and isolating plasmids having a structural gene for alkaline phosphatase using the phoA mutant E. coli SB44 by a method of isolating plasmids containing phoA genes from a mixture of plasmids, some without and one or more with a phoA gene, comprising transforming phoA mutant E. coli SB44 bacteria by the mixture of plasmids; isolating and cloning each transformed bacterium; forming a transformant bacterial culture for each; incubating each culture under conditions under which alkaline phosphatase will be expressed in the presence of a phoA gene which codes for said phosphatase; and determining the presence of alkaline phosphatase in each incubated culture which presence indicates, in turn, the presence of a plasmid containing the phoA gene.

In yet another aspect, these objects have been attained by providing bacteria transformed with the plasmids of this invention, as well as methods by which the proteins coded by these plasmids can be expressed.

In a further aspect, these objects have been attained by providing a method for modifying the plasmids of this invention to code for proteins other than alkaline phosphatase and then expressing the DNA sequence which codes the new protein.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

In FIGS. 1 and 3, the following symbols are used to denote recognition sequences for restriction enzymes:
EcoRI
HindIII
BamHI
SalI
PstI
XhoI Other abbreviations are respectively:
Ap$^+$ and Ap$^-$ — ampicillin resistance and ampicillin sensitivity
Tc$^+$ and Tc$^-$ — tetracycline resistance and tetracycline sensitivity
Pho$^+$ and Pho$^-$ — capability for the synthesis of alkaline phosphatase present and not present
Bp — Base pairs.

Figure 1:
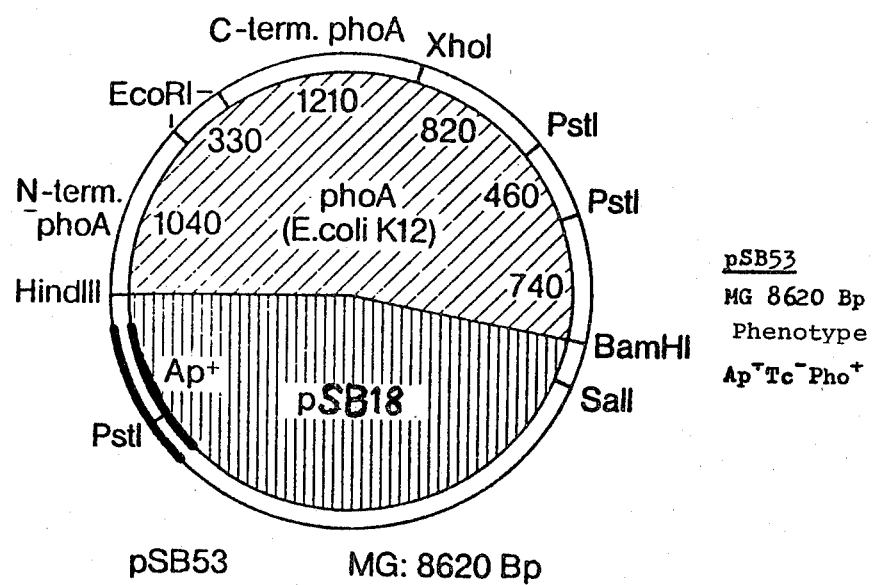
FIG. 1 displays the restriction maps of plasmids pSB53, pSB86 and pSB87.
Figure 1:
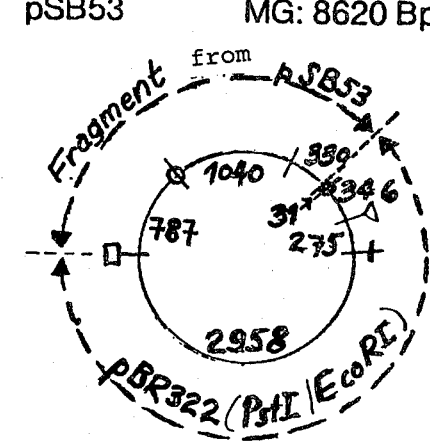
Figure 1:
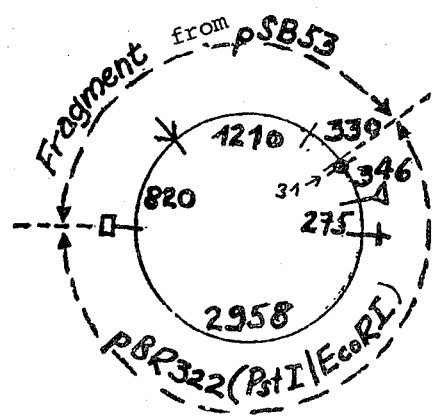

The numerical values cited in the plasmid diagrams refer to molecular weights in bp.

DETAILED DISCUSSION

The present invention provides a heretofore unknown mutant of a well-transformable E. coli strain, E. coli K12 HB101 using a mutation procedure known per se. In this mutant, the structural gene for alkaline phosphatase (phoA) is inactivated. This mutant is employed, e.g., using the above-mentioned methods of DNA cloning, for the transformation with in vitro recombined DNA (i.e., recombinant plasmids) and for the subsequent selection of cell clones containing recombined DNA having genes for alkaline phosphatase.

The aforementioned mutation method can be suitably effected using N-nitroso compounds including those customarily employed for mutations. Suitable N-nitroso compounds include, for example, nitrosoureas and nitrosoquanidines. 1-Nitroso-3-nitro-1-methylguanidine has proved to be an especially suitable compound. The conventional mutation methods which are employable, for example, are disclosed by Edward A. Adelberg et al. in Biochemical and Biophysical Research Communications 18, 788 (1965), whose disclosures are incorporated by reference herein.

This invention also provides plasmid vectors containing a DNA sequence for alkaline phosphatase, as well as plasmid vectors containing a DNA sequence coding an N-terminal amino acid sequence of an alkaline phosphatase, the sequences, when complemented in the proper reading phase by fragments of foreign DNA coding for a desired peptide sequence and containing a stop codon will induce the biosynthesis of corresponding fused proteins in cells transformed with the recombinant plasmids.

The phoA-gene-containing plasmids of this invention can be produced by reacting chromosomal DNA (containing the phoA gene) from wild-type bacteria and an antibiotic-resistant plasmid with restriction endonucleases for which the plasmid has cutting sites. After subsequent linkage of the cutting sites with DNA ligase, plasmids which have been recombined with structural genes for alkaline phosphatase can be isolated according to the process described above, using the phoA mutant E. coli SB44 obtained from E. coli K12 HB101. From these plasmids, additional plasmids can be prepared which likewise contain phoA genes. For this purpose, subfragments are excised from these plasmids again using restriction enzymes. These subfragments, containing the phoA gene, are recombined with antibiotic-resistant vector plasmids in the presence of DNA ligase.

The term "wild-type bacteria" as used herein means bacteria customarily employed by one skilled in the art for microbiological processes. Bacteria of the wild-type strains E. coli K12 and Serratia marcescens have proved to be especially suitable.

The plasmids of this invention can be obtained, for example, by cutting the total DNA from E. coli K12 wild-type bacteria and the pBR313 plasmid which conveys resistance against ampicillin, with the restriction endonuclease BamHI, and then recombining with DNA ligase. The aforementioned phosphatase-negative mutant (E. coli SB44) is incubated with the ligase-treated DNA mixture under conventional transformation conditions [for instance by W. Goebel et al. in J. Bacteriology 123, 658 (1975), whose disclosure is incorporated by reference herein] during which step a small portion of the cells (about 1 out of $10^4$) absorbs plasmid DNA. By multiplication in an ampicillin-containing medium, wherein the ampicillin-sensitive mutant cannot grow, the transformed cells are enriched. After plating out the thus-enriched cell population on agar plates with a very low phosphate content and incubating at 37°, thus maximally inducing phosphatase formation, the thus-obtained individual colonies are layered over with a solution of p-nitrophenyl phosphate. Phosphatase-positive colonies hydrolyze this substance to yellow p-nitrophenol [K. Kreuzer et al, "Genetics" 81: 459-468 (1975)]. On the average, one yellow colony is found among about 10,000 colorless colonies. From these pho+ colonies, plasmid DNA is isolated according to the method by G. O. Humphreys et al, Biochem. Biophys. Acta 383: 457-463 (1975), whose disclosure is incorporated by reference herein. The analysis of the thus-obtained plasmid, called pSB47, by cleavage with BamHI and gel electrophoresis of the cleavage products showed that it consists of the starting plasmid pBR313 and an additional DNA fragment (molecular weight about 11 megadaltons). The proof that pSB47 contains a phosphatase gene is provided by a renewed transformation of the phosphatase mutant E. coli SB44 with the plasmid. It was found thereby that all ampicillin-resistant colonies were also phosphatase-positive. Since pBR313 does not have a gene for alkaline phosphatase, it had to be located on the additional recombined DNA fragment of the molecular weight of 11 megadaltons.

The pSB51 plasmid is prepared in a quite similar manner to that of pSB47. The sole difference are that chromosomal DNA from Serratia marcescens is used instead of E. coli DNA; that pWB2 was utilized as the vector; and that the chromosomal DNA as well as the vector were cut with the restriction endonuclease HindIII. pSB51 contains, in addition to the pWB2 vector, a DNA fragment of a molecular weight of 2.5 megadaltons, on which a phosphatase gene was determined similarly as described above. Moreover, a comparison with authentic phosphatases from E. coli and S. marcescens by means of disk electrophoresis shows that the E. coli cells with pSB51 plasmid produce an enzyme identical to S. marcescens phosphatase. This proves that the 2.5 DNA fragment having a molecular weight of 2.5 megadaltons in pSB51 stems from Serratia DNA and carries a Serratia phosphatase gene.

Also, a subsequent modification of the plasmids is possible in some cases without loss of essential properties. Thus, it is possible, for example, to divide the fragment of mol. wt. 11 megadaltons in pSB47 into several partial fragments by cleavage with the restriction endonuclease HindIII. The second-largest fragment (mol. wt. 3.1 megadaltons) of these carries the phosphatase gene. This was coupled by ligase linkage with subsequent transformation and selection as above to a vector (pSB18) derived from pBR322 [F. Bolivar et al, "Gene" 2: 95–113 (1977)], in which the EcoRI section site of pBR322 is missing. From this vector, by reaction with HindIII and BamHI, a partial fragment of mol. wt. 0.18 megadalton unnecessary for replication and selection can be removed and replaced by the subfragment with the phosphatase gene from pSB47. The result is the phosphatase plasmid pSB53.

Another plasmid, pSB50, can be prepared in a manner similar to that used for the pSB47 plasmid. The difference resides merely in using pWB2 as the starting vector and reacting it together with chromosomal DNA from E. coli with the restriction endonuclease HindIII. Bacterial strains with the thus-obtained pSB50 plasmid produce alkaline phosphatase just as those obtained with pSB47.

The present invention also relates to a process for preparing novel strains of bacteria (i.e., transformants) which comprises incubating competent cells of the respective bacterial strain with the phosphatase plasmids under transformation conditions using conventional methods, and isolating the antibiotic-resistant cells from the thus-obtained cell population, e.g., by killing off the resistant cells, i.e., those not transformed by recombinant plasmids, by treatment with an appropriate antibiotic such as ampicillin.

With the thus-obtained bacterial strains containing genes for alkaline phosphatase in their plasmids, larger amounts of alkaline phosphatase can be produced than heretofore possible. For this purpose, the strains are fermented in a medium with a minimum phosphate content and the thus-formed phosphatase is isolated according to conventional methods. See, for example, the review paper of T. W. Reid et al. cited on page 2, line 28, whose disclosure is incorporated by reference herein. In particular, the alkaline phosphatases from Serratia marcescens and from E. coli are prepared. It has been made possible, for example, to effect the production of alkaline phosphatase of Serratia marcescens by E. coli SB44, i.e., by using Serratia marcescens DNA as the source of the phoA gene, and E. coli SB44 as the receptor bacterium for the recombinant plasmid.

Table I contains a summary of the concentrations of alkaline phosphatase, expressed in units per millimeter of culture liquor. These values were determined for various strains containing phosphatase plasmids, as well as for the corresponding control strains, without or with chromosomal phosphatase gene. The determinations were under conditions wherein the formation of alkaline phosphatase is maximally highly stimulated (induction by low phosphate content of the medium). It has been found in all instances that the presence of one of the phosphatase plasmids effected a significant increase in the phosphatase content, namely up to 11 times the value for the strains having only one chromosomal phosphatase gene. This holds true, in particular, also for Serratia marcescens which is an example of a host cell capable of receiving E. coli plasmids.

The plasmid containing *E. coli* phosphatase gene known from J. Bacteriol. 120:970-973 (1974) is present only in 1-2 copies, whereas the plasmids of this invention are present in up to 20 copies per cell.

TABLE I
Phosphatase Production of Bacteria with phoA Plasmids (*)

| Host Cell | Plasmid | Origin of phoA Gene in Plasmid | Phosphatase Activity |
|---|---|---|---|
| *E. coli* SB44 | — | — | 0 |
| (phoA mutant) | pSB47 | *E. coli* | 11.0 |
|  | pSB50 | " | 12.5 |
|  | pSB53 | " | 20.0 |
|  | pSB51 | *S. marcescens* | 19.5 |
|  | pSB60 | *E. coli* | 20.1 |
| *E. coli* HB101 | pWB 2 | (Vector without phoA Gene) | 5.0 (+) |
|  | pSB47 | *E. coli* | 18.0 |
|  | pSB50 | " | 13.0 |
| *E. coli* K12 | — | — | 2.5 |
| (wild type) | pSB47 | *E. coli* | 11.0 |
|  | pSB50 | " | 13.6 |
|  | pSB51 | *S. marcescens* | 19.5 |
| *S. marcescens* | — | — | 4.1 |
| (wild type) | pSB51 | *S. marcescens* | 44.0 |
|  | pSB53 | *E. coli* | 19.6 |

(+) *E. coli* HB101 without or with other vectors has the same phosphatase activity.
(*) LP Medium [K. Kreuzer et al., "Genetics" 81: 459-468 (1975)] supplemented with 0.2% Casamino Acids was inoculated with 5% of a fully grown culture of the respective plasmid-containing strain and shaken for 23 hours at 37° ($E_{500}$ = 7.0). Thereafter 1 ml of culture liquor was shaken with 0.01 ml of toluene for 20 minutes at 37°. In the toluene-treated cell suspension, alkaline phosphatase was determined according to Kreuzer et al. The phosphatase activity is indicated in units per ml of culture liquor. One unit is the amount of enzyme effecting under testing conditions an increase in extinction $E_{410}$ = 1.0 per minute.

The recombined plasmids producible according to the process of this invention are novel chemical substances that are definable with respect to their structure.

The plasmids of this invention can also be utilized with special advantages as plasmid vectors for the expression of eucaryotic proteins in *Escherichia coli* and other bacteria by the formation of fusion proteins with N-terminal partial sequences from alkaline phosphatases. The advantages provided thereby as compared to other plasmid vectors will be explained in greater detail below.

The processes for the in vitro recombination of DNA with the use of plasmid or phage vectors, and the transfer of the thus-formed hybrid molecules into suitable host cells by transformation or transfer have made it possible also to transfer DNA from higher eucaryotic cells to bacteria in a replicatable form (K. N. Timmis in "Process in Molecular and Subcellular Biology," F. E. Hahn et al., 6:1–58, Springer, publishers (1978), whose disclosure is incorporated by reference herein). However, the thus-transformed bacterial cells were normally incapable of synthesizing the proteins corresponding to the genes present on the transferred eucaryotic DNA.

The expression of genes from higher eucaryotic cells in bacteria is possible only by the use of special plasmid vectors constructed for instance in such a way that the eucaryotic gene can be integrated into a bacterial gene already present on the plasmid, the native gene effecting by itself the synthesis of a suitable, well characterized bacterial protein. If the eucaryotic DNA is integrated with the correct orientation and in the correct triplet pattern, the thus-equipped bacterial cells transformed by such a hybrid molecule produce a fusion protein. The latter begins, from the amino terminus, with part of the bacterial amino acid sequence and continues toward the carboxy terminus with the amino acid sequence corresponding to the integrated eucaryotic DNA. From the fusion protein, it is then possible to obtain the ducaryotic protein by means of suitable enzymatic or protein-chemical cleaving methods, for example by cleavage of a methionine present at the linkage site with cyanogen bromide.

The first example for such a polypeptide synthesis was the microbial production of the peptide hormone somatostatin (14 amino acids) obtained in the form of a fusion protein with the bacterial enzyme β-galactosidase [K. Itakura et al., "Science" 198:1056–1063 (1977)]. In a similar way, the microbial synthesis of the A- and B-chains of human insulin has recently been accomplished, wherein, as in the case of somatostatin, fully synthetic DNA sequences were coupled to a gene for β-galactosidase (DOS's Nos. 2,848,051; 2,848,052 and 2,848,053). Additional examples include the preparation of bacterial strains which produce rat proinsulin in the form of a fusion protein with the bacterial enzyme β-lactamase [L. Villa-Komaroff et al., Proc. Natl. Acad. Sci. USA 75: 3727–3731 (1978)] and an ovalbumin-similar protein with sequences of β-galactosidase [O. Mercereau-Puijalon et al., Nature 275: 505–510 (1978)]. This method of microbial polypeptide synthesis should also be applicable to the production of other eucaryotic peptides and proteins which in part are accessible only with much difficulty using other methods. Such polypeptides include, for example, human growth hormone, interferon, viral proteins for active immunization, specific antibodies, etc.

The success of microbial polypeptide syntheses with the use of recombinant DNA depends quite essentially on the properties of the vectors employed. In the aforementioned examples, plasmid vectors were utilized wherein the foreign DNA was integrated into genes for β-galactosidase or β-lactamase. These two bacterial proteins, however, also exhibit disadvantages as fusion partners for the expression of foreign DNA. Fusion proteins with β-galactosidase can be produced just as the original enzyme itself by corresponding media composition (induction with β-galactosides) in relatively large amounts ($10^5$ molecules per cell), but the proteins are not excreted, for example, by the cells into the medium and can thus be isolated only by cell breakdown. β-Lactamase and the fusion proteins derived therefrom are transported during the synthesis into the periplasmatic space through the cell membrane, making a simple isolation possible. (No cell breakdown is required.) However, here the yield is only minor (about 100 molecules per cell).

The present invention thus also concerns the preparation of plasmid vectors whereby it is possible to incorporate foreign DNA into alkaline phosphatase genes. Cells transformed with such hybrid plasmids or hybrid phages formed from such plasmid vectors then produce fusion proteins, the amino acid sequence of which is determined by the nucleotide sequence of the gene for alkaline phosphatase as well as that of the integrated foreign DNA.

The use of these vectors represents an improvement as compared with the above-cited methods of microbial synthesis of eucaryotic peptides and proteins. Alkaline phosphatases as fusion partners in the expression of eucaryotic genes combine in themselves the advantages of β-galactosidase and β-lactamase. They can be high-induced just as β-galactosidase by corresponding media composition (low phosphate concentration) and are transported, just as β-lactamase, through the cell membrane into the periplasmatic space (Summary, T. W.

Reid, I. B. Wilson in "The Enzymes" Ed. P. D. Boyer, Acad. Press, 1971 IV: 373–415).

In order to use phosphatase vectors in the aforedescribed way for the production of fusion proteins, they must be constructed so that the restriction sequence, over which the foreign DNA to be expressed is to be integrated, is, if at all possible, not present at all, anywhere outside of the phosphatase gene in the remaining portion of the vector. Thus, the restriction endonuclease will cleave the plasmid only at the single desired phosphatase gene site. The plasmids pSB53 and pSB86 described in Examples 4 and 6 meet these conditions. When the fusion protein is later cleaved to release the desired foreign protein this can be accomplished by using either the method described for the preparation of somatostatin (Itakura et al., cited on page 18, line 17), which consists in cleaving a methionine residue with cyanogen bromide, or by the method described in German Patent Applications Nos. P 29 22 496.2, P 30 12 170.2, P 30 12 169.8, which consists in sequential cleavage with specific proteases.

It has been shown that the gene for alkaline phosphatase from *E. coli* K12 is present in the pSB47 plasmid on a DNA fragment having a molecular weight of 4600 bp, which can be liberated by simultaneous cleavage with the restriction endonucleases BamHI and HindIII. This fragment was coupled to the pSB18 plasmid by reaction with DNA ligase. The latter plasmid effects resistance against ampicillin and tetracycline, and had been produced from pBR322 by elimination of the EcoRI sequence. Prior to the reaction with ligase, pSB18 was likewise cut with HindIII and BamHI, thus removing a small partial fragment which is concomitantly responsible for the tetracycline resistance. After transformation of the phosphatase-negative mutant SB44 with the DNA mixture, cells were selected which were ampicillin-resistant, tetracycline-sensitive and phosphatase-positive. From these, the pSB53 plasmid could be isolated. The phoA fragment contained therein can also be obtained directly from chromosomal DNA from *E. coli* K12 by cleavage with HindIII and BamHI. Thus, an essential prerequisite for the isolation of pSB53 and the remaining vectors is the use of the phosphatase-negative mutant *E. coli* SB44.

The restriction map of pSB53 for the enzymes HindIII, BamHI, EcoRI, PstI, XhoI and SalI is illustrated in FIG. 1. It could be shown that, by exchanging the EcoRI fragment of 330 bp in pSB53 against another EcoRI fragment, the gene for alkaline phosphatase is inactivated. This gene, therefore, must lie in the range of the EcoRI restriction sequences. By partial cleavage of pSB53, two fragments were obtained having the molecular weights of 2157 and 2360 bp, of which one (2157 bp) comprises the sequences shown in FIG. 1 with 787, 1040, and 330 bp, whereas the other (2360 bp) consists of the sequences with 330, 1210, and 820 bp. The two fragments were cloned with the aid of pBR 322 in *E. coli* SB44, resulting in the plasmids pSB86 and pSB87 illustrated in FIG. 1. Both plasmids no longer possess an intact gene for alkaline phosphatase, from which the conclusion must be drawn that both EcoRI restriction sequences present on pSB53 lie in this gene. The PstI sequences in pSB53 are outside of the phoA gene.

It has been demonstrated that the influencing of the phosphatase formation by the phosphate concentration of the medium is a positively controlled process, and that an activator, bound to a promoter region of this gene, is required for the transcription of the phoA gene. A substantial component of the activator is the product of the phoB gene [H. Morris et al, J. Bacteriol. 119: 583–592 (1974); C. Pratt and A. Torriani, "Genetics" 85: 203–208 (1977)].

One of the two plasmids pSB86 and pSB87, both of which no longer contain a complete phosphatase gene, should contain the binding sequence for the activator and thus also the gene region corresponding to the N-terminal end of the alkaline phosphatase. In a strain having an intact chromosomal phoA gene, this plasmid should reduce the phosphatase formation, since it competes with the chromosomal gene for the activator and binds the latter partially, yet can produce no phosphatase.

We have now discovered that the pSB87-transformed strain of *E coli* HB101 forms the same quantity of phosphatase as *E. coli* HB101 without plasmid (respectively 5.6 units per milliliter of culture liquor, measured under the same conditions as described in the note of the foregoing table); whereas HB101 transformed with pSB86 produces only about 25–30% of this quantity (1.5 U/ml). It can be seen therefrom that the activator binding sequence and thus also the beginning of transcription of the phoA gene are on pSB86. The transcription direction of the phoA gene in pSB53 thus points from the HindIII sequence to the BamHI sequence (clockwise direction in FIG. 1). The gene starts with the end corresponding to the amino terminus of the phosphatase, on the left-hand side from the EcoRI fragment with 330 bp, between the EcoRI and the HindIII sequence, and extends over the two EcoRI sequences into the XhoI/EcoRI fragment with 1210 bp. An exchange of the EcoRI fragment with 330 bp in pSB53 against another DNA fragment thus makes it possible, with correct orientation and correct triplet pattern, to produce fusion proteins which begin from the amino terminus with a partial sequence of the alkaline phosphatase from *E. coli*.

Another vector permitting the preparation of the same fusion proteins as pSB53 is the pSB86 plasmid (FIG. 1) which still contains the amino-positioned part of the phoA gene. Also, plasmids containing at this point only the EcoRI/HindIII fragment (1040 bp) from pSB53 should fulfill the same purpose. From pSB53 or pSB47, Pst fragments could be obtained with the entire phoA gene and could be utilized for the construction of novel vectors, to name only a few of the numerous combination possibilities. By similar testing using other restriction endonucleases, it would probably be possible to find other linkage sites for the preparation of fused genes having partial sequences of the gene for alkaline phosphatase. As can be seen, the requirement for the use of a plasmid containing such a fused gene in protein production by the general recombinant DNA method, is that the fused gene contain a DNA sequence which codes the N-terminal sequence of an alkaline phosphatase.

Additional possibilities for the construction of vectors into which hybrid genes can be formed and by which fusion proteins can be formed, i.e., expression vectors, can be derived by the subsequent introduction of restriction sequences into the gene for alkaline phosphatase. Various processes which should make this possible have been described. Thus, the formation of EcoRI sequences in a phage vector has been attained, for example, by in vitro mutation after methylation [B.

Gronenborn and I. Messing, "Nature" 272: 375–377 (1978)].

A method having a much broader applicability has been described by F. Heffron, M. So, and B. I. McCarthy [Proc. Natl. Acad. Sci. USA 75: 6012–6016 (1978)], wherein a synthetic oligonucleotide containing the desired restriction sequence is inserted in a gene present on a plasmid vector. For this purpose the vector DNA is reacted with a suitable endonuclease, which is capable of cleaving the ring-shaped double-strand DNA at many different locations, under incomplete cleavage conditions, so that linear molecules of full length are produced to a great part. These molecules are separated from the remaining reaction products by a suitable method, e.g., preparative gel electrophoresis. Any single-strand termini which may be present are converted into a complete double-strand termini using DNA polymerase. With T4 ligase, the synthetic restriction sequence is coupled to the termini of the DNA. After cleaving with the corresponding restriction endonuclease to produce complementary single-strand termini, another reaction in DNA ligase is conducted for purposes of ring closure. During this step, ring molecules are produced which can contain the synthetic restriction sequence at all those sites where cleavage was previously effected by endonuclease. By transformation of a suitable host cell, in this case the phoA mutant *E. coli* SB44, and selection of transformants which have not become positive for the respective gene, i.e., here remained pho⁻, cell clones are obtained from which plasmids can be isolated which have integrated the synthetic restriction sequence at various defined sites into the plasmid gene (here the phoA gene).

Heffron et al utilized pancreas deoxyribonuclease for the partial cleavage. In the same way, it is also possible to use restricted endonucleases which cut very frequently and therefore also, with high probability, in the gene to be modified. These include especially the restriction endonucleases which recognize sequences of 4 base pairs. They frequently exhibit the additional advantage over pancreas DNase of directly yielding complete double-strand termini. An up-to-date overview of the conventional restriction endonucleases is provided, for example, by R. I. Roberts [in: "Methods in Enzymology" 68: 27; S. P. Colowick and N. O. Kaplan Ed.; Academic Press, New York (1979)].

The usability of the process of this invention for the construction of novel expression vectors is proven and demonstrated by the production of the pSB90 plasmid (Example 9) obtained by the introduction of a synthetic oligonucleotide with the recognition sequence for BamHI restriction endonuclease into the phoA gene of the pSB60 plasmid. pSB60 was prepared from pSB53 (see Example 4) by elimination of the BamHI sequence already present therein, so that pSB90 contains only the one, newly introduced BamHI sequence. For the partial cleavage of pSB60, HaeIII restriction endonuclease was utilized. Various synthetic oligonucleotides suitable for the same application have been disclosed [see, for example, R. I. Rothstein et al, in: "Methods in Enzymology" 68: 98; S. P. Colowick and N. O. Kaplan Ed.; Academic Press, New York (1979)]and are, in part commercially available.

The following plasmids and plasmid-containing bacterial strains have been deposited with the American Type Culture Collection (ATCC) in Rockville, Md., U.S.A. on July 16, 1979 (deposit number):

Plasmid pWB2: (ATCC 40013)
Plasmid pBR313: (ATCC 40014)
Plasmid pBR322: (ATCC 40015)
Plasmid pSB18: (ATCC 40016)
Plasmid pSB47: (ATCC 40017)
Plasmid pSB50: (ATCC 40018)
Plasmid pSB51: (ATCC 40019)
Plasmid pSB53: (ATCC 40020)
Plasmid pSB87: (ATCC 40021) and
*Escherichia coli* SB44 with pSB47: (ATCC 31540)
*E. coli* SB44 with pSB51: (ATCC 31541)
*E. coli* SB44 with pSB53: (ATCC 31542)
*Serratia marcescens* wild type with pSB51: (ATCC 31543)

Furthermore, the following microorganisms were deposited with the "Deutsche Sammlung von Mikroorganismen (DSM)": [German Collection of Microorganisms] in Göttingen, Federal Republic of Germany on July 16, 1979 (deposit number):

*Escherichia coli* SB44: (DSM 1606)
*Escherichia coli* HB101: (DSM 1607)
*Serratia marcescens* wild type: (DSM 1608)
and on July 16, 1980 (deposit number):
*E. coli* SB44 with pSB60: (DSM 1873)
*E. coli* SB44 with pSB86: (DSM 1874)
*E. coli* SB44 with pSB90: (DSM 1875)

For the microorganism *Escherichia coli* K12 wild type, deposit has been effected since Nov. 26, 1973 under the DSM deposit number DSM 498.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Isolation of phoA Mutant *E. coli* SB44

25 ml of L-medium containing 10 g/l tryptone (Difco), 5 g/l yeast extract, and 5 g/l NaCl [E. S. Lennox, "Virology" 1: 190–206 (1955)] was inoculated with 0.25 ml of an overnight culture of *E. coli* K12 HB101 [H. W. Boyer, D. Roulland-Dussoix, "J. Mol. Biol." 41: 459–472 (1969)] in L-medium and incubated in a temperature-controllable shaker at 37° C. Upon attainment of the exponential growth phase ($E_{500}$ about 1.5), samples of respectively 5 ml were taken from the culture and combined with respectively 0.1 ml of a corresponding dilution of a freshly prepared solution of 5 g/l 1-nitroso-3-nitro-1-methylguanidine (NNMG) so that final concentrations of 0 (control), 10, 25, 50, and 100 µg/ml of NNMG were produced. The samples were incubated for 10 minutes at 37° and immediately thereafter removed by centrifuging at +4° C., twice washed with respectively 5 ml of cold sterile NaCl solution (9 g/l), and resuspended in respectively 5 ml of NaCl solution. By plating out dilution series on agar plates (1.5% agar in L-medium) the live germ numbers were determined. A comparison with the value of the control sample without NNMG showed that the mutation batch with 10 µg/ml NNMG had a survival rate of 0.5% especially favorable for mutant selection.

From a dilution of this batch, containing about 1,000 cells per ml, samples of respectively 0.1 ml were applied to agar plates (0.15% agar) with LP-medium [K. Kreuzer et al., "Genetics" 81: 459–468 (1975)] supplemented with 20 mg/l of L-proline and 20 mg/l of L-leucine. In this medium, the synthesis of alkaline phosphatase is derepressed due to the low phosphate content.

After incubation for 48 hours at 37° C. the plates, on which individual colonies had been formed, were layered over with a solution of 5 mg/ml of p-nitrophenyl phosphate in 1-molar tris-HCl buffer, pH 8.0. Individual colonies which did not exhibit a yellow coloration within a few minutes were off-inoculated and further tested by quantitative determination of the formation of alkaline phosphatase, as described in the table.

Two phosphatase-negative mutants were found, denoted as E. coli SB43 and SB44. As shown in Example 3, the pSB51 plasmid effects in the SB44 E. coli mutant the formation of the alkaline phosphatase from S. marcescens. For this reason, pSB51 must contain, on the one hand, a phoA gene from S. marcescens and the E. coli mutant SB44 must be a phoA mutant. Since the SB43 mutant after transformation with pSB51 does not become phosphatase-positive, it must be a phoB mutant. This correlation was confirmed by the transformation of authentic phoA and phoB mutants with the plasmids described in the following examples.

EXAMPLE 2

(a) Preparation of Plasmid pSB47

Plasmid pBR313 was utilized as the vector, this plasmid effecting resistance against ampicillin and tetracycline [F. Bolivar et al., "Gene" 2: 75–93 (1977)]. The pBR313 plasmid was isolated according to the method set forth therein (ATCC No. 40014). High-molecular chromosomal DNA from E. coli K12 wild type bacteria was isolated by following the phenol extraction method by Saito et al. [Biochem. Biophys. Acta 72: 619–629 (1963)], but omitting the RNase digestion. Both types of DNA were dialyzed against DNA buffer (45 millimoles tris-HCl, 0.1 millimole EDTA, pH 7.9) and further used in this form. The BamHI was obtained, just as the T4 ligase (100 units/ml) from the company Biolabs (Beverly, Md., U.S.A.). Plasmid and chromosomal DNA were reacted with BamHI restriction endonuclease (obtained from Biolabs, 4,000 units/ml). The BamHI reaction mixture had the following composition: 15 µl pBR313 (250 µg/ml DNA), 45 µl chromosomal DNA from E. coli K12 (180 µg/ml), 60 µl BamHI reaction buffer (20 millimoles tris-HCl, 60 millimoles KCl, 20 millimoles MgCl$_2$, 20 millimoles dithiothreitol, pH 7.5), 60 µl BamHI (1:40 dilution). The mixture was incubated for 60 minutes at 37° C. and heated for 10 minutes to 65° to stop the enzymatic reaction. The enzyme dilution necessary for quantitative conversion was determined in a preliminary experiment wherein the degree of conversion was determined of ring-shaped plasmid DNA into linear plasmid DNA by gel electrophoresis in 0.7% agarose [J. F. Morrow et al., Proc. Natl. Acad. Sci. USA 71: 1743–1747 (1974)].

The above reaction mixture (180 µl) was combined with 40 µl of T4 ligase buffer (660 millimoles tris-HCl, 66 millimoles MgCl$_2$, 100 millimoles dithiothreitol, pH 7.6), 40 µl of ATP (4 millimoles), 2 µl of T4 ligase, and 138 µl of H$_2$O (total volume 400 µl). The mixture was incubated for 16 hours at 13° C., extracted twice with respectively 400 µl of phenol which had previously been saturated with TES buffer (50 mmol tris-HCl, 50 mmol NaCl, 5 mmol EDTA, pH 8.0), and dialyzed free of phenol against DNA buffer.

(b) Transformation and Selection of pho+ Cells

With the ligase reaction, competent cells of the phoA mutant E. coli SB44 (Example 1) were transformed.

To produce the competent cells, a slightly modified method by Lederberg et al. was utilized [J. Bacteriol. 119: 1072–1074 (1974)]. The cells were grown as in Example 1 in L-medium (100 ml) up to the opt. density E$_{500}$=0.8, removed by centrifuging, and suspended in 100 ml of MgCl$_2$ solution (100 mmol). After 20 minutes at 0° C. and centrifuging, the cells were taken up in 50 ml of CaCl$_2$ solution (30 mmol) and centrifuged off after another 20 minutes at 0° C., suspended in 5 ml of CaCl$_2$ (30 mmol), and stored in ice until further use.

For transformation purposes [W. Goebel and R. Bonewald, J. Bacteriol. 123: 658–665 (1975)], 200 µl of ice-cooled ligase reaction and 400 µl of competent cells were mixed, heated for 50 seconds in a 38° C. water bath, and stored for 60 minutes at 0° C. After the addition of 8 ml of L-medium, the cells were incubated for 2 hours at 37°, then transferred into L-medium (100 ml) with 50 µg/ml ampicillin, and incubated for another 16 hours at 37° C. From this ampicillin enrichment, phosphatase-positive individual colonies were isolated by the same method as used in Example 1 for the isolation of phosphatase-negative mutants. Among about 10,000 colorless colonies, respectively one yellow one was found.

(c) Isolation and Characterization of pSB47

According to conventional methods [G. O. Humphreys et al., Biochem. Biophys. Acta 383: 457–463 (1975)], a plasmid of a molecular weight of 16.8 megadaltons could be isolated from the yellow colonies; this plasmid was called pSB47 and showed, after cutting with BamHI in agarose gel 2 DNA bands of a molecular weight of 5.8 megadaltons (linear pBR313) and 11 megadaltons (chromosomal pho fragment). By transformation of the mutants indicated in Example 1, it was demonstrated that pSB47 contains a phoA gene.

EXAMPLE 3

Preparation of Plasmid pSB51

The vector plasmid pWB2, possessing a cutting site for the restriction endonuclease HindIII and conveys resistance against ampicillin and colicin E1 [W. Boidol et al., "Molec. Gen. Genet." 152: 231–237 (1977)] was isolated according to methods known from the literature [G. O. Humphreys et al., Biochem. Biophys. Acta 383: 457–463 (1975)]. The process differs from the one described in Example 2 in that 45 µl of chromosomal DNA (135 µg/ml) from Serratia marcescens wild type was utilized in place of E. coli DNA, and that the vector pWB2 and the DNA from Serratia marcescens were cut with the restriction endonuclease HindIII. An Rk mixture, consisting of 15 µl, of pWB2 (360 µg/ml DNA), 45 µl of chromosomal DNA (135 µg/ml), 60 µl of HindIII reaction buffer (20 mmol tris-HCl, 20 mmol mercaptoethanol, 20 mmol MgCl$_2$, 180 mmol NaCl, pH 7.4), and 60 µl of a dilute HindIII solution was incubated as described in Example 2 for 60 minutes at 37° C. and heated for 10 minutes to 65° C. to stop the enzymatic reaction. The additional reaction takes place as in Example 2. From the phosphatase-positive colonies, isolated as in Example 2, a plasmid called pSB51, molecular weight 9.6 megadaltons, could be isolated which, after reaction with HindIII showed in gel electrophoresis 2 DNA bands of molecular weight 7.1 megadaltons (linear pWB2) and 2.5 megadaltons (chromosomal fragment). By transformation, it could be shown as in Example 3 that pSB51 contains only a phoA gene.

The alkaline phosphatase produced from *E. coli* SB44 (pSB51) was compared by disk electrophoresis with the corresponding enzymes from *E. coli* K12 and *S. marcescens*. For this purpose, the raw enzymes were isolated by osmotic shock from the induced cells [A. Torriani, in "Procedures in Nucleic Acid Research" pp. 224-235, G. L. Cantoni and D. R. Davies, Ed., Harper and Row, publishers, New York (1966)].

In detail, the cells (about 1.5 g moist weight) were harvested, from 0.5 l of a shaken culture prepared as indicated in the table, by centrifuging, washed three times with 10 mmol tris-HCl, pH 7.7, and suspended in 30 ml of a cane sugar solution (0.5 mol saccharose, 30 mmol tris-HCl, 0.5 mmol EDTA, pH 8.0). The suspension was stirred for 10 minutes at room temperature. The cells were removed by centrifuging, suspended in 30 ml of water of 3°-5° C., stirred for 10 minutes, and again removed by centrifuging. From the supernatant portion, the raw enzyme was precipitated with $(NH_4)_2SO_4$ (85% saturation), the protein precipitate was dissolved in 0.6 ml, 37 mmol tris-HCl, pH 8.5, and dialyzed against the same buffer.

For the disk electrophoresis of the raw phosphatases [H. R. Maurer, "Disk-Elektrophorese" (Disk Electrophoresis), publishers Walter de Gruyter, Berlin (1968)], acrylamide flat gels were utilized, consisting of 10% separating gel in 0.185 mol tris-HCl, pH 8.5, and 5% collective gel in 0.037 mol tris-HCl, pH 8.5 with 0.037 mol tris-borate, pH 8.5 as the electrophoresis buffer. Separation was conducted at 450 volts (4 hours). The phosphatase bands were made visible in the gel by a specific color reaction [O. Gabriel, in "Methods in Enzymol." 22: 590, W. B. Jakoby, Ed., Academic Press (1971)], based on a hydrolysis of the α-naphthol phosphate to α-naphthol and formation of an azo dye.

Figure 2:
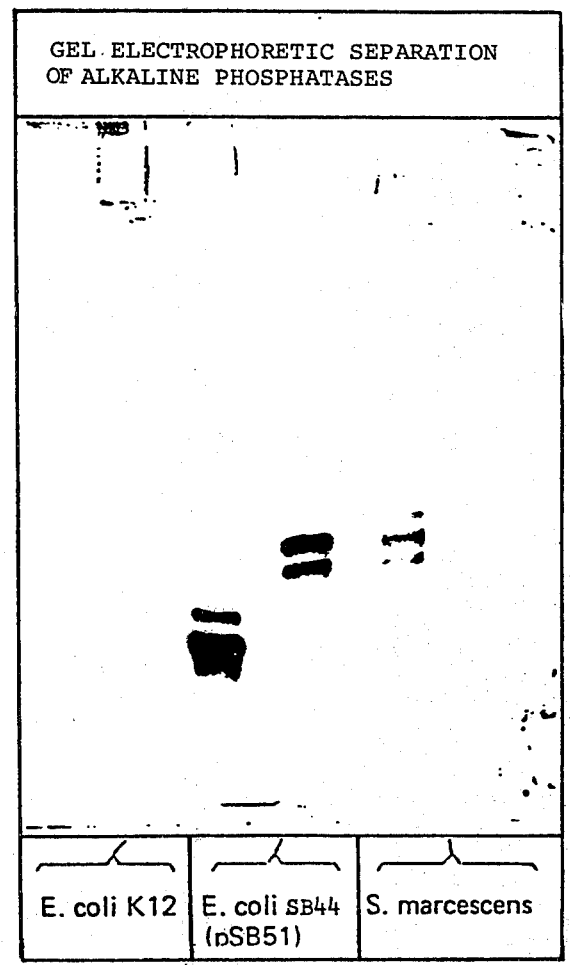
FIG. 2 depicts the results of a gel electrophoretic separation of alkaline phosphatases produced by several bacteria.

The enzyme preparations from the two reference strains resulted in the known patterns of respectively 3 closely adjacent phosphatase bands which clearly differed from one another (the bands from the enzyme of *S. marcescens* run markedly more slowly than those of the *E. coli* K12 enzyme). The enzyme from *E. coli* SB44 (pSB51) showed a band pattern coinciding with the pattern of the *S. marcescens* enzyme (see FIG. 2).

EXAMPLE 4

Preparation of Plasmic pSB53

(a) Preparation of Plasmid pSB18 pSB18 was prepared from plasmid pBR322 by the removal of the EcoRI restriction sequence. pBR322 has been described by Bolivar et al. ["Gene" 2: 95-113 (1977)] and was isolated as set forth therein. The DNA was further used as a solution in 45 mmol tris-HCl, 0.1 mmol EDTA, pH 7.9 (DNA buffer).

The restriction endonuclease EcoRI was isolated according to methods known from the literature [P. J. Greene et al., in "Methods in Molecular Biology" 7: 7, R. B. Wickner Ed., Marcel Dekker Inc., New York (1974)]. T4-DNA polymerase (5,000 units/ml) was obtained from the company PL-Biochemicals Inc. (Milwaukee, Wis., U.S.A.) and T4-DNA ligase (100 units/ml) was obtained from Biolabs (Beverly, Md., U.S.A.).

A reaction mixture consisting of 10 μl pBR322 (620 μg/ml), 10 μl EcoRI reaction buffer (300 mmol tris-HCl, 30 mmol $MgCl_2$, pH 7.5) and 10 μl of a dilute EcoRI solution was incubated for 60 minutes at 37° C. and heated for 10 minutes to 65° C. to stop the enzymatic reaction. The enzyme dilution required for quantitative conversion was determined in a preliminary experiment, wherein the degree of conversion from ring-shaped into linear plasmid DNA was determined by gel electrophoresis in 0.7% agarose [J. F. Morrow et al., in "Proc. Natl. Acad. Sci. USA" 71: 1743-1747 (1974)].

The batch (30 μl volume) was combined with 10 μl of polymerase buffer (600 mmol tris-HCl, 80 mmol $MgCl_2$, 100 mmol mercaptoethanol, pH 7.5), respectively 10 μl of 500 μmol solutions of 2'-deoxyadenosine 5'-triphosphate (dATP), 2'-deoxyguanosine 5'-triphosphate (dGTP), 2'-deoxythymidine 5'-triphosphate (dTTP), and 2'-deoxycytidine 5'-triphosphate (dCTP), as well as 10 μl of T4-DNA polymerase (1:2000 dilution) and 10 μl of water. The mixture (100 μl volume) was heated for 30 minutes to 37° C. and, for stopping purposes, for 10 minutes to 70° C.

Thereafter 15 μl of ligase buffer (660 mmol tris-HCl, 66 mmol $MgCl_2$, 100 mmol dithiothreitol, pH 7.6), 15 μl of ATP (4 mmol), 2 μl of T4-DNA ligase, and 18 μl of $H_2O$ were added thereto. The mixture (150 μl volume) was incubated for 16 hours at 13° C. and heated for 10 minutes to 65° C.

To convert residual pBR322 into the poorly transforming linear form, the mixture was reacted once again as indicated above with EcoRI (reaction volume 250 μl), then extracted twice with respectively 250 μl of phenol previously saturated with DNA buffer, and dialyzed free of phenol against DNA buffer (300 μl final volume).

Competent cells were produced from the strain *E. coli* K12 HB101 [H. W. Boyer, D. Roulland-Dussoix, "J. Mol. Biol." 41: 459-472 (1969)]. To prepare the competent cells, a slightly modified method by Lederberg et al. was utilized ["J. Bacteriol." 119: 1072-1074 (1974)]. The cells were grown as in Example 1 in L-medium (100 ml) up to the opt. density $E_{500}=0.8$, removed by centrifuging, and suspended in 100 ml of $MgCl_2$ solution (100 mmol). After 20 minutes at 0° C. and centrifuging, the cells were taken up in 50 ml of $CaCl_2$ solution (30 mmol) and removed by centrifuging after another 20 minutes at 0° C., suspended in 5 ml of $CaCl_2$ (30 mmol), and stored in ice until further use. For transformation purposes, 200 μl of the DNA solution obtained after ligase reaction and 400 μl of competent cells were mixed together, heated for 50 seconds in a 38° C. water bath, and stored for 60 minutes at 0° C. After adding 8 ml of L-medium (10 g/l tryptone [Difco], 5 g/l of yeast extract, 5 g/l of NaCl) [E. S. Lennox, "Virology" 1: 190-206 (1955)], the cells were incubated for 2 hours at 37° C., then transferred into L-medium (100 ml) with 50 μl/ml of ampicillin, and incubated for another 16 hours at 37° C. From this ampicillin enrichment, individual colonies were isolated in the usual way on agar plates, which colonies were resistant to ampicillin (100 μg/ml) and tetracycline (25 μg/ml). From 4 individual colonies, plasmid DNA was isolated according to known methods [G. O. Humphreys et al., Biochem. Biophys. Acta 383: 457-463 (1975)]. In all 4 cases, a plasmid was isolated which differed from the starting plasmid pBR322 merely by the missing restriction sequence for EcoRI. This plasmid was designated pSB18.

(b) Preparation of Plasmid pSB53

The restriction endonuclease HindIII was isolated according to conventional methods [H. O. Smith, K. W. Wilcox, J. Mol. Biol. 51: 379–391 (1970) and P. Philippsen, R. E. Streek, H. G. Zachau, Eur. J. Biochem. 45: 479–488 (1974)]. The restriction endonuclease BamHI was obtained from Biolabs.

A reaction mixture consisting of 2 μl of pSB18 (350 μg/ml), 8 μl of pSB47 (40 μg/ml), 10 μl of HindIII reaction buffer (20 mmol tris-HCl, 20 mmol mercaptoethanol, 20 mmol $MgCl_2$, 180 mmol NaCl, pH 7.4), 5 μl of dilute HindIII solution, and 5 μl of BamHI solution was heated for 60 minutes to 37° C. and for 10 minutes to 65° C. The enzyme dilutions necessary for quantitative splitting were determined previously as in Example 1 by gel electrophoresis.

The mixture was combined with 10 μl of ligase buffer, 10 μl of ATP (4 mmol), 1 μl of T4 ligase, and 50 μl of $H_2O$. Then the mixture was incubated for 16 hours at 13° C., extracted twice with phenol, and dialyzed against DNA buffer.

The transformation of the phosphatase-negative mutant SB44 with the DNA solution and the selection of ampicillin-resistant and phosphatase-positive individual colonies took place as described in Example 2(b).

From several of these colonies, a plasmid having a molecular weight of 8600 bp, designated as pSB53, could be isolated, which was divided by simultaneous cleavage with the restriction endonucleases HindIII and BamHI into 2 fragments with the molecular weights of 4020 bp and 4600 bp. The larger fragment proved to be identical, in analysis by gel electrophoresis, with a fragment produced in the dual digestion of pSB47 as well as pSB47 with HindIII and BamHI, which therefore must carry the gene for alkaline phosphatase. The second fragment from pSB53 (4020 bp) was identical with the larger fragment formed from pSB18 by dual digestion.

EXAMPLE 5

Properties of pSB53

To produce a restriction diagram, the pSB53 plasmid was reacted with the restriction endonucleases EcoRI, HindIII, BamHI, PstI, SalI, BglII, KpnI, XhoI, and XbaI. EcoRI, HindIII, and BamHI were constituted by the same batches as in Example 1, the remaining enzymes were obtained from Biolabs. The standard reaction mixtures contained 10 μl of pSB53 (170 μg/ml), 10 μl of reaction buffer, and 10 μl of enzyme dilution. Reaction buffers as set forth in Example 4 and/or as indicated by the enzyme producer were utilized. The enzyme dilutions required for quantitative reaction were determined in preliminary experiments by cleavage of the DNA of the bacteriophage λ. The reaction mixtures were incubated for 60 minutes at 37° C. and, after the addition of 10 μl of stop solution, another 30 minutes at 37° C. The stop solution contained 100 mmol EDTA, 400 mg/ml of saccharose, and 0.5 mg/ml of proteinase K (Merck, Darmstadt). The reaction products were analyzed by electrophoresis in flat gels from 0.7% agarose [J. F. Morrow et al. in "Proc. Natl. Acad. Sci. USA" 71: 1743–1747 (1974)] or 3.5% polyacrylamide [T. Maniatis et al., "Biochemistry" 14: 3787–3794 (1975)]. The determination of the molecular weights of the DNA fragments was effected by comparison with calibration fragments obtained according to J. G. Sutcliffe ["Nucl. Acids Res."5: 2721–2728 (1978)] from pBR322 (data in base pairs, bp).

The enzymes HindIII, BamHI, SalI, and XhoI resulted in each case in a linear band of identical molecular weight, whereas two and three smaller bands, respectively, were produced by EcoRI and PstI. BglII, KpnI, and XbaI did not cleave pSB53.

Of the bands obtained as in Example 4(b) by the simultaneous cleavage with HindIII and BamHI, that of a molecular weight of 4020 bp exhibited the cutting sites for PstI and SalI known from the structure of pBR322, whereas the band of a molecular weight of 4600 bp derived from chromosomal DNA of E. coli K12 was divided into 2 fragments of 2580 bp and 2020 bp by XhoI. The fragment with 2580 bp disintegrated with EcoRI into three subfragments (1210, 1040, and 330 bp), whereas the fragment with 2020 bp resulted with PstI in three subfragments (820, 740, and 460 bp). From these data, as well as from additional, comparative dual reactions with HindIII/EcoRI and BamHI/PstI, the restriction diagram for pSB53 illustrated in FIG. 1 could be derived.

To prove the location of the phoA gene in the zone of the EcoRI cutting sites of pSB53, the EcoRI fragment with 330 bp was replaced by another EcoRI fragment with 3600 bp carrying the proA gene from E. coli K12. This fragment can be obtained from the pSB37 plasmid wherein it is present as hybrid plasmid with pBR313 [F. Bolivar et al., "Gene" 2: 75–93 (1977)]. By the incorporation of pSB37, the proline-deficient strain E. coli K12 HB101 and the phosphatase-negative mutant E. coli SB44 derived therefrom become proline-prototrophic, as well as ampicillin- and tetracycline-resistant, whereas pSB53 only effects resistance against ampicillin.

A mixture of 5 μl of pSB53 (170 μg/ml), 5 μl of pSB37 (90 μg/ml), 10 μl of reaction buffer, and 10 μl of EcoRI solution was reacted as in Example 4(a) and stopped by heating. The further reaction of the DNA mixture with T4 ligase, transformation of the strain E. coli SB44, and the enrichment of ampicillin-resistant cells was conducted as set forth in Example 4(b). The cells from 2 ml of this culture broth were removed by centrifuging, suspended in 2 ml of sterile NaCl solution (9 g/l), diluted with NaCl solution, and plated out on agar plates in various stages of dilution with minimum medium without proline (1.0 g/l $NH_4Cl$, 0.25 g/l $MgSO_4.7H_2O$, 3.0 g/l $KH_2PO_4$, 7.0 g/l $Na_2HPO_4.2H_2O$, 4.0 g/l glucose, 0.5 g/l NaCl, 20 mg/l leucine, 1 mg/l vitamin $B_1$, pH 7.0 [M9 medium]) and incubated at 37° C. until individual colonies have been established. Tetracycline-sensitive colonies were identified by transferring same with the aid of the stamping technique to agar plates with 10 μg/ml of tetracycline. These were tested for the capability of forming alkaline phosphatase and all proved to be phosphatase-negative.

The plasmid DNA which could be isolated from the colonies having the phenotype $Pro^+$, $Pho^-$, $Ap^+$, $Tc^-$ and which was designated pSB54 was cleaved as above with EcoRI and analyzed by gel electrophoresis. Two DNA bands could be detected, molecular weight 8290 bp and 3600 bp, identical to the corresponding bands from pSB53 and pSB37. The fragment with 330 bp from pSB53, in contrast thereto, was no longer present in pSB54.

EXAMPLE 6

Preparation of Plasmids pSB86 and pSB87

Five reaction mixtures, consisting of respectively 5 μl of pSB53 (170 μg/ml), 5 μl of water, 10 μl of EcoRI reaction buffer, and 10 μl of various EcoRI dilutions, were incubated for 60 minutes at 37° C. and heated for 10 minutes to 65° C. in order to stop the reaction. Enzyme dilutions were used of 1:200, 1:250, 1:320, 1:400, and 1:500. In a preliminary experiment it was found that the dilution of 1:200 is just barely sufficient for quantitative cleavage, whereas the remaining dilutions only provided a partial reaction.

The reaction mixtures of respectively 30 μl were combined with respectively 20 μl of PstI reaction buffer (30 mmol tris-HCl, 150 mmol NaCl, 30 mmol $MgCl_2$, pH 7.0), as well as respectively 10 μl of PstI solution (Biolabs, dilution 1:20). It was determined in a preliminary test that the amount of PstI is sufficient for quantitative reaction. The mixtures were incubated for 60 minutes at 37° C., then mixed for stopping the reaction with respectively 15 μl of a solution of EDTA (100 mmol) and saccharose (400 mg/ml) and separated by electrophoresis in gels of 0.7% agarose (see Example 5).

While the reaction mixture with the EcoRI dilution of 1:200 showed five DNA bands having the molecular weights of 3980, 2030, 1827, 460, and 330 bp, the remaining mixtures contained additionally two and three bands, respectively, with 2157, 2360, and 4180 bp.

The double band of 2157 and 2360 bp was isolated from the gel by electrophoretic adsorption on hydroxylapatite according to the method by H. F. Tabak and R. A. Flavell, "Nucleic Acid Res." 5: 2321–2332 (1978). Subsequently the DNA was eluted from the hydroxylapatite with 1-molar sodium phosphate buffer, dialyzed, precipitated with 2 volumes of ethanol, and dissolved in DNA buffer.

The pBR322 plasmid was reacted in the same way with EcoRI and PstI, but only under conditions leading to quantitative cleavage. Of the thus-produced two DNA fragments, the larger one (3610 bp) was isolated as described above by electrophoretic adsorption on hydroxylapatite.

A mixture of the fragments isolated in this way from pSB53 and pBR322 was reacted with T4 ligase as in Example 4(b). With the reaction product, the phosphatase-negative strain E. coli SB44 was transformed; from the transformation reaction mixture, resistant cells were enriched in L-medium with 10 μg/ml of tetracycline.

Tetracycline-resistant individual colonies were tested by stamping on L-medium with 50 μg/ml ampicillin and on LP-medium [K. Kreuzer et al., "Genetics" 81: 459–468 (1975)] for ampicillin resistance and phosphatase formation. All cells were phosphatase-negative; about 70% was ampicillin-resistant, and 30% was ampicillin-sensitive.

From the ampicillin-resistant cells, a plasmid could be isolated, designated as pSB86, by means of conventional methods, this plasmid resulting, by cutting with EcoRI and PstI, in three bands of 3610 bp (from pBR322) as well as 1827 and 330 bp (from pSB53). From the ampicillin-sensitive cells, pSB87 was isolated, resulting with EcoRI and PstI in three bands of 3610, 2030, and 330 bp. The restriction diagrams of pSB86 and pSB87 are illustrated in FIG. 1.

EXAMPLE 7

Preparation of Plasmid pSB50

(a) In Vitro DNA Linkage

The vector plasmid pWB2, possessing a cutting site for HindIII restriction endonuclease and conveying resistance against ampicillin and colicin El [W. Biodol, G. Siewert, W. Lindenmaier, G. Luibrand, W. Goebel, "Molec. Gen. Genet." 152: 231–237 (1977)] was isolated according to methods known from the literature ]G. O. Humphreys et al., "Biochem. Biophys. Acta" 383: 457–463 (1975)]. High-molecular chromosomal DNA from E. coli K12 wild-type bacteria was isolated by following the phenol extraction method by Saito et al. ["Biochem. Biophys. Acta" 72: 619–629 (1963)], but omitting the RNase digestion. Both kinds of DNA were dialyzed against DNA buffer (45 mmol tris-HCl, 0.1 mmol EDTA, pH 7.9) and further used in this form. The isolation of HindIII restriction endonuclease has been disclosed ["J. Mol. Biol." 51: 379–391 (1970) and "Eur. J. Biochem." 45: 479–488 (1974)]. T4 Ligase (100 units/ml) was obtained from Biolabs (Beverly, Md., U.S.A.).

A reaction mixture consisting of 15 μl of pWB2 (360 μg/ml DNA), 45 μl of chromosomal DNA (180 μg/ml), 60 μl of HindIII reaction buffer (20 mmol tris-HCl, 20 mmol mercaptoethanol, 20 mmol $MgCl_2$, 180 mmol NaCl, pH 7.4) and 60 μl of a dilute HindIII solution was incubated for 60 minutes at 37° C. and heated for 10 minutes to 65° C. in order to stop the enzymatic reaction. The enzyme dilution necessary for a quantitative conversion was determined in a preliminary experiment wherein the degree of conversion of ring-shaped into linear plasmid DNA was determined by gel electrophoresis in 0.7% agarose [J. F. Morrow et al., "Proc. Natl. Acad. Sci. USA" 71: 1743–1747 (1974)].

The above reaction mixture (180 μl) was combined with 40 μl of T4 ligase buffer (660 mmol tris-HCl, 66 mmol $MgCl_2$, 100 mmol dithiothreitol, pH 7.6), 40 μl of ATP (4 mmol), 2 μl of T4 ligase, and 138 μl of $H_2O$ (total volume 400 μl). The mixture was incubated for 16 hours at 13° C., extracted twice with respectively 400 μl of phenol, previously saturated with TES buffer (50 mmol tris-HCl, 50 mmol NaCl, 5 mmol EDTA, pH 8.0), and dialyzed free of phenol against DNA buffer.

(b) Transformation and Selection of pho+ Cells

By means of the ligase reaction, competent cells of the phoA mutant E. coli SB44 (Example 1) were transformed.

To produce the competent cells, a slightly modified process by Lederberg et al. was employed [J. Bacteriol. 119: 1072–1074 (1974)]. The cells were grown as in Example 1 in L-medium (100 ml) up to an opt. density $E_{500}=0.8$, centrifuged, and suspended in 100 ml of $MgCl_2$ solution (100 mmol). After 20 minutes at 0° C. and centrifuging, the cells were taken up in 50 ml of $CaCl_2$ solution (30 mmol) and, after another 20 minutes at 0° C., centrifuged, suspended in 5 ml of $CaCl_2$ (30 mmol), and stored in ice until further use.

For transformation purposes [W. Goebel and R. Bonewald in "J. Bacteriol." 123: 658–665 (1975)], 200 μl of ice-cooled ligase reaction product and 400 82 1 of competent cells were mixed together, heated for 50 seconds in a 38° C. water bath, and stored for 60 minutes at 0° C. After adding 8 ml of L-medium, the cells were incubated for 2 hours at 37° C., then transferred into L-medium (100 ml) with 50 μg/ml of ampicillin, and incubated for another 16 hours at 37° C. From this ampicillin enrichment, phosphatase-positive individual colonies were isolated with the same method employed in Example 1 for the isolation of phosphatase-negative mutants. Among about 10,000 colorless colonies, respectively one yellow one was found.

(c) Isolation and Characterization of pSB50

According to conventional methods [G. O. Humphreys et al., "Biochem. Biophys. Acta" 383: 457–463 (1975)] a plasmid having a molecular weight of 22 megadaltons could be isolated from the yellow colonies, this plasmid being designated as pSB50. This plasmid was reacted as above with HindIII restriction endonuclease and analyzed by gel electrophoresis in 0.7% agarose [J. F. Morrow et al., "Proc. Natl. Acad. Sci. USA" 71: 1743–1747 (1974)]. Two DNA bands were observed, of which the more rapidly migrating one (molecular weight 7.1 megadaltons) was identical with linear pWB2. The second band had a molecular weight of about 15 megadaltons. By transformation with pSB50, all mutants mentioned in Example 1 became phosphatase-positive. Therefore, pSB50 must carry a phoA gene as well as a phoB gene, which are in close adjacency on the E. coli chromosome.

EXAMPLE 8

Conversion of phoA Plasmids into Bacterial Strains

Plasmids pSB47, pSB51, pSB53, and pSB50 described in Examples 2, 3, 4, and 7 were converted into E. coli SB44 and into the phosphatase-positive strains E. coli K12, E. coli HB101, and S. marcescens. For this purpose, the cells were rendered competent as described in Example 2 and transformed with the isolated DNA. The thus-obtained plasmid-containing strains are compiled in the table, wherein also the phosphatase production is indicated under derepressed conditions and compared with the corresponding values of the starting strains.

EXAMPLE 9

Preparation of Plasmid pSB90

(a) Elimination of the BamHI sequence in pSB53

The same reaction sequence was employed as in the preparation of pSB18 (Example 4[a]) with the difference that pSB53 was used as the starting plasmid and was cut with BamHI instead of with EcoRI.

A reaction mixture consisting of 10 μl of pSB53 (490 μg/ml), 10 μl of BamHI buffer (see Example 2[a]), and 10 μl of BamHI (1:40 dilution, obtained from Biolabs) was incubated for 60 minutes at 37° C. and heated for 10 minutes to 65° C. for stopping purposes.

For the further reaction with DNA polymerase and T4 ligase, the same reaction components were added as in Example 4(a) under the same conditions.

To convert residual pSB53 into the poorly transforming linear form, the mixture was once again reacted with BamHI as above (reaction volume 250 μl) and then extracted with phenol and dialyzed as in Example 4(a).

The transformation of E. coli SB44 and the selection of ampicillin-resistant and phosphatase-positive individual colonies was effected as in Example 2(b). From this, a plasmid denoted by pSB60 could be isolated which differed from pSB53 only by the missing restriction sequence for BamHI.

(b) Introduction of a BamHI Sequence into the Gene for Alkaline Phosphatase on pSB60

A reaction mixture consisting of 50 μl of pSB60 (440 μg/ml), 100 μl of HaeIII reaction buffer (20 mmol tris-HCl, 20 mmol NaCl, 20 mmol MgCl₂, 20 mmol mercaptoethanol, 300 μg/ml of cattle serum albumin, pH 7.4) and 150 μl of a 1:200 dilution (2.85 units) of the restriction endonuclease HaeIII (Biolabs) was incubated for 60 minutes at 37° C.; the reaction was terminated by adding 100 μl of stopping solution (100 mmol EDTA, 40% saccharose). The enzyme dilution was determined in a preliminary experiment as in Example 2(a) and was dimensioned so that about ⅓ of the ring-shaped plasmid DNA was cut only once and thus resulted in linear molecules of full length.

The reaction mixture was separated as in Example 5 by electrophoresis in 0.7% agarose gels, the band with the full-length linear DNA was identifid by comparison with pSB60 cut with HindIII and was excised from the gel. The DNA was eluted by following conventional processes [H. O. Smith in: "Methods in Enzymology" 65: 371 et seq.; S. P. Colowick and N. O. Kaplan Ed.; Acedemic Press, New York (1980)] by electrophoresis in a dialyzing hose from the gel and purified by phenol extraction and chromatography from DEAE cellulose.

A reaction mixture consisting of 10 μl of a solution with 100 μg/ml of the synthetic BamHI sequence d(C-C-G-G-A-T-C-C-G-G) (Collaborative Research Inc., Waltham, Mass., U.S.A.), 3 μl of reaction buffer (660 mmol tris-HCl, 66 mmol MgCl₂, 100 mmol dithiothreitol, pH 7.6), 5 μl of ATP solution (4.0 mmol), 7 μl of water, and 5 μl of polynucleotide kinase (1,380 units/ml, Boehringer Mannheim) was incubated for 60 minutes at 37° C. The reaction mixture (30 μl) was combined with 100 μl of the linear DNA purified by electrophoresis (40 μg/ml), 15 μl of ATP (4 mmol), 15 μl of reaction buffer as above, 15 μl of water, and 25 μl of T4 ligase (2.5 units, Biolabs). The mixture (200 μl total volume) was incubated for 16 hours at 13° C., extracted with phenol, and dialyzed against DNA buffer (45 mmol tris-HCl, 0.1 mmol EDTA, pH 7.9).

The solution was reacted as in Example 2 with BamHI restriction endonuclease and thereupon again with T4 ligase. The transformation of the mutant E. coli SB44 with the DNA solution, the enrichment of ampicillin-resistant cells, and the identification of phosphatase-negative colonies from this enrichment was effected as set forth in Example 2 and Example 1, respectively.

Figure 3:
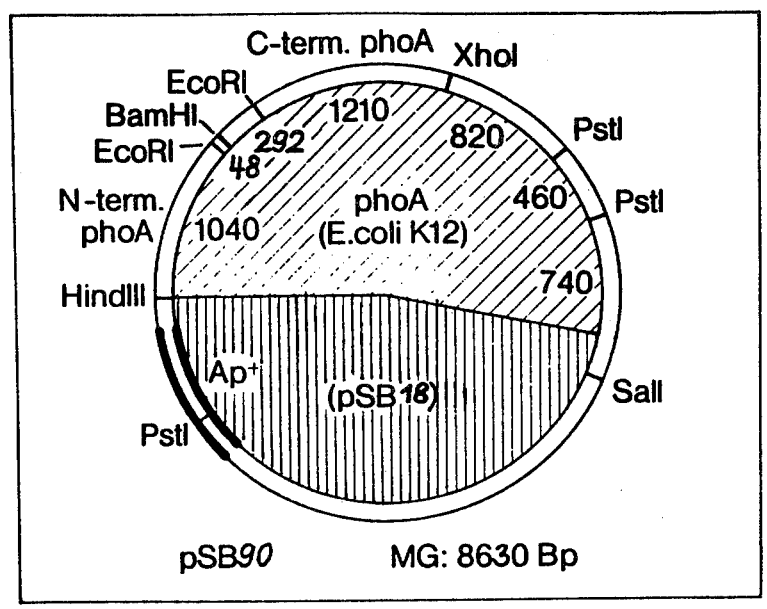
FIG. 3 displays the restriction map of plasmid pSB90.

From an ampicillin-resistant, phosphatase-negative colony, a plasmid could be isolated which was designated by pSB90. The characterization of pSB90 took place similarly as described in Example 5 for pSB53, by reaction with various restriction endonucleases and analysis of the reaction products inclusive molecular weight determination by gel electrophoresis. FIG. 3 shows the restriction diagram of pSB90 derived from these data. As expected, this diagram differs from the restriction diagram for pSB53 (FIG. 1) only by the position of the BamHI sequence located between the two EcoRI sequences in pSB90, which likewise are within the phosphatase gene (see Example 5).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Substantially biologically pure phoA negative type mutant E. coli SB44 (DSM 1606), which is substantially incapable of in vivo recombination.

2. A process for preparing substantially biologically pure phoA negative type mutant E. coli SB44 (DSM 1606) having a mutation in the structural gene (phoA) for alkaline phosphatase and which is substantially incapable of in vivo recombination, comprising contacting substantially biologically pure E. coli K12 HB101 (DSM 1606) with an N-nitroso compound and subsequently separating the substantially biologically pure phoA mutant E. coli SB44 from any concomitantly-produced phoB mutants mutated in a regulatory gene (phoB).

3. A process of claim 2, comprising contacting E. coli K12 HB101 with 1-nitroso-3-nitro-1-methylguanidine.

4. A method of isolating plasmids containing phoA genes from a mixture of plasmids, some without and one or more with a phoA gene, comprising transforming substantially biologically pure phoA negative type mutant E. coli SB44 (DSM 1606), which is substantially incapable of in vivo recombination, with the mixture of plasmids, identifying phosphatase-positive colonies from the transformation mixture and isolating plasmid-DNA containing a phoA gene from these colonies.

5. A method for preparing the plasmid pSB86, comprising reacting to completion the plasmid pSB53 with PstI, isolating the thus-produced DNA fragment of about 2157 base pairs containing the N-terminal end of the phoA gene, partially cleaving the fragment with EcoRI, and coupling the resultant subfragment containing the N-terminal of the phoA gene with the vector plasmid pBR322.

6. A method for preparing the plasmid PSB53, comprising cutting the antibiotic-resistant vector plasmid pSB18 and the pho A plasmid pSB47 or pSB50 with the restriction endonucleases BamHI and Hind III to form a mixture of DNA; treating the resulting mixture of DNA fragments with DNA ligase to link the fragments; transforming substantially biologically pure pho A negative type mutant E. coli SB44 (DSM 1606) which is substantially incapable of in vivo recombination with the linked fragments; and identifying and isolating and isolating the phosphatase-positive colonies from the transformed mixture containing pSB53.

7. A method for preparing plasmids containing a phoA gene, comprising reacting an antibiotic-resistant plasmid and chromosomal DNA from a wild-type bacteria with a restriction endonuclease, linking the terminal sites with DNA ligase to form a recombinant DNA, transforming substantially biologically pure phoA mutant E. coli SB44 (DSM 1606) with the DNA mixture, identifying phosphatase-positive colonies from the transformation mixture and isolating plasmid-DNA containing a phoA gene from these colonies.

8. A method of claim 7 for preparing the plasmid pSB47, comprising reacting the antibiotic-resistant plasmid pBR313 and chromosomal DNA from E. coli K12 wild type with the restriction endonuclease HindIII.

9. A method of claim 7 for preparing the plasmid pSB50, comprising reacting the antibiotic-resistant plasmid pWB2 and chromosomal DNA from E. coli K12 wild type with the restriction endonuclease HindIII.

10. A method of claim 7 for preparing the plasmid pSB51, comprising reacting the antibiotic-resistant plasmid pWB2 and chromosomal DNA from Serratia marcescens wild type with the restriction endonuclease HindIII.

11. A substantially biologically pure plasmid vector with which bacteria can be transformed to contain 10–20 copies of said vector per cell; which contains a first DNA sequence (phoA) coding for alkaline phosphatase; which is antibiotic resistant; and which is prepared by the method of claim 7.

12. Plasmid pSB47, a substantially biologically pure plasmid of claim 11.

13. Plasmid pSB50, a substantially biologically pure plasmid of claim 11.

14. Plasmid pSB51, a substantially biologically pure plasmid of claim 11.

15. Plasmid pSB53, a substantially biologically pure plasmid of claim 6.

16. Plasmid psB60, a substantially biologically pure plasmid of claim 11.

17. A substantially biologically pure plasmid vector containing a first DNA sequence which continuously sequentially codes only a portion of the polypeptide sequence of an alkaline phosphatase, said polypeptide sequence containing the N-terminal amino acid of the alkaline phosphatase and the length of said portion being sufficient that the fusion protein coded by the combination of said DNA sequence and the adjacent sequence in reading phase therewith, will be transported into the periplasmatic space upon culturing of a bacterial cell transformed with said plasmid vector under effective culturing conditions.

18. Plasmid pSB86, a substantially biologically pure plasmid of claim 10.

19. A substantially biologically pure plasmid vector of claim 11 or 17, wherein said first DNA sequence is modified to contain a heterologous restriction sequence.

20. Plasmid pSB90, a substantially biologically pure plasmid of claim 19.

21. A substantially biologically pure plasmid vector of claims 11 or 17, wherein said first DNA sequence is followed in reading phase by a DNA sequence which codes for another polypeptide.

22. A substantially biologically pure plasmid vector of claim 21, wherein said other polypeptide is heterologous.

23. A method for preparing a novel strain of E. coli or S. marcescens which lacks resistance to a particular antibiotic and has been transformed with a plasmid containing a phoA gene and a gene yielding resistance to said antibiotic, comprising incubating transformable cells of the first bacterial strain with said plasmid under transformation conditions, and isolating from the cell population cells which are resistant to said antibiotic, wherein said plasmid vector is one with which bacteria can be transformed to contain 10–20 copies of said vector per cell; which contains a first DNA sequence (phoA) coding for alkaline phosphatase; which is antibiotic resistant; and which is prepared by the method of claim 7.

24. A transformed bacterial strain prepared by the method of claim 23.

25. A method of preparing alkaline phosphatase, which comprises fermenting in a medium suitable for alkaline phosphatase production by bacteria and having a minimum phosphate content, a biologically pure transformant E. coli or S. marcescens bacterium transformed with a plasmid vector with which bacteria can be transformed to contain 10–20 copies of said vector per cell; which contains a first DNA sequence (phoA) coding for alkaline phosphatase; which is antibiotic resistant; and which is prepared by the method of claim 7.

26. A method of claim 25 for preparing alkaline phosphatase from *S. marcescens* using *S. marcescens* transformed with plasmid pSB51 or *E. coli* SB44 transformed with plasmid pSB51, comprising fermenting said transformed bacteria in a medium having a minimum phosphate content, and isolating the thus-formed phosphatase.

27. A method of claim 25 for preparing alkaline phosphatase from *E. coli* using *E. coli* SB44 transformed with plasmid pSB47 or plasmid pSB53, comprising fermenting said transformed bacteria with a medium having a minimum phosphate content, and isolating the thus-formed phosphatase.

28. A bacterium transformed with a plasmid vector containing a first DNA sequence which continuously sequentially codes only a portion of the polypeptide sequence of an alkaline phosphatase, said polypeptide sequence containing the N-terminal amino acid of the alkaline phosphatase and the length of said portion being sufficient that the fusion protein coded by the combination of said DNA sequence and the adjacent sequence in reading phase therewith will be transported into the periplasmatic space upon culturing of a bacterial cell transformed with said plasmid vector under effective culturing conditions.

29. A bacterium of claim 28 transformed with said plasmid vector wherein said first DNA sequence is modified to contain a heterologous restriction sequence.

30. A bacterium of claim 28 transformed with said plasmid vector wherein said first DNA sequence is followed in reading phase by a DNA sequence which codes for another polypeptide.

31. A bacterium of claim 30 transformed with said plasmid vector wherein said other polypeptide is heterologous.

32. A bacterial culture comprising a cloned bacterium transformed with a plasmid vector containing a first DNA sequence which continuously sequentially codes only a portion of the polypeptide sequence of an alkaline phosphatase, said polypeptide sequence containing the N-terminal amino acid of the alkaline phosphatase and the length of said portion being sufficient that the fusion protein coded by the combination of said DNA sequence and the adjacent sequence in reading phase therewith will be transported into the periplasmatic space upon culturing of a bacterial cell transformed with said plasmid vector under effective culturing conditions.

33. *E. coli* Sb44 transformed with plasmid pSB47.
34. *E. coli* SB44 transformed with plasmid pSB50.
35. *E. coli* SB44 transformed with plasmid pSB51.
36. *E. coli* SB44 transformed with plasmid pSB53.
37. *E. coli* HB101 transformed with plasmid pSB47.
38. *E. coli* HB101 transformed with plasmid pSB50.
39. *E. coli* K12 transformed with plasmid pSB47.
40. *E. coli* K12 transformed with plasmid pSB50.
41. *E. coli* transformed with plasmid pSB51.
42. *S. marcescens* wild-type transformed with plasmid pSB51.
43. *S. marcescens* wild-type transformed with plasmid pSB53.
44. *E. coli* SB44 transformed with plasmid PSB60.
45. *E. coli* SB44 transformed with plasmid pSB86, a bacterium of claim 28.
46. *E. coli* SB44 transformed with plasmid pSB90.

* * * * *